United States Patent [19]

Siler et al.

[11] 4,435,829

[45] Mar. 6, 1984

[54] APPARATUS FOR RADIOGRAPHIC EXAMINATION OF PIPE WELDS

[75] Inventors: Dan R. Siler, Clinton; Harold D. Trimble, Riverdale, both of Utah

[73] Assignee: Johnson Service Company, Milwaukee, Wis.

[21] Appl. No.: 492,692

[22] Filed: May 12, 1983

Related U.S. Application Data

[63] Continuation of Ser. No. 265,419, May 19, 1981, abandoned.

[51] Int. Cl.³ .................... B62B 13/16; G01N 23/02
[52] U.S. Cl. ................................ 378/60; 104/138 R; 105/365; 250/358.1
[58] Field of Search ......... 378/60; 104/138 G, 138 R, 104/139; 105/365; 280/8; 16/26; 250/358.1

[56] References Cited

U.S. PATENT DOCUMENTS

| 300,156 | 6/1884 | Starr | 280/8 |
| 616,411 | 12/1898 | Dimmitt | 16/26 |
| 2,360,036 | 10/1944 | Boucher | 378/60 |
| 3,794,340 | 2/1974 | Tartabini et al. | 104/138 G |

Primary Examiner—Alfred E. Smith
Assistant Examiner—T. N. Grigsby
Attorney, Agent, or Firm—John Phillip Ryan; Joseph J. Jochman, Jr.; Larry L. Shupe

[57] ABSTRACT

An x-ray probe carrier for the inspection of circumferential welds in cylindrical pipes includes a carriage supported on omnidirectional ball transfers for movement along the bottom of a pipe section. A centrally mounted adjustable probe holder is preset to coincide with the centerline of the pipe for single exposure x-ray examination of a full circumferential weld. The probe is maintained centered during travel along the pipe and is automatically recentered after travel through a horizontal bend. The probe holder is easily adjustable for use in a wide range of pipe sizes.

5 Claims, 4 Drawing Figures

APPARATUS FOR RADIOGRAPHIC EXAMINATION OF PIPE WELDS

This application is a continuation of application Ser. No. 265,419, filed May 19, 1981, now abandoned.

BACKGROUND OF THE INVENTION

This invention relates to apparatus for use in the internal examination of pipes and, more particularly, to the x-ray examination of welded joints in cylindrical pipes. The device of the present invention is particularly useful in the x-ray examination of welds in shorter pipe sections during shop fabrication, as opposed to field inspection of welds in relatively longer pipeline sections.

Radiographic inspection devices for use in examining circumferential welds from the inside of cylindrical pipes are well known in the art. Such devices vary widely in complexity from self-propelled, fully automatic equipment to manually-operated, relatively simple devices. Irrespective of their complexity, the devices of the prior art may be classified in two basic types.

One type utilizes a series of circumferentially spaced wheels which are biased against the interior cylindrical pipe surface to inherently maintain the radiographic device on the centerline of the pipe as it travels therein. A fully automated version of a device of this kind is shown in U.S. Pat. No. 4,006,359. A similar type of device is disclosed in U.S. Pat. No. 3,492,477 and, like the apparatus shown in the previously identified patent, this device is primarily intended for use in relatively long pipeline sections. These devices are, however, far too complex for use during shop fabrication of welded pipe sections. A manually operated version of the same type of inspection device is shown in U.S. Pat. No. 2,607,012. Because this device requires operator access from outside the pipe, its use is necessarily restricted to relatively shorter pipe sections. However, even this device is too cumbersome for rapid installation and operation in the x-ray inspection of one or more welds in a relatively short pipe section.

The other general type of prior art device comprises a wheeled carriage adapted to travel along the bottom of a pipe interior. Typical prior art embodiments of this kind are shown in U.S. Pat. Nos. 3,547,040 and 3,949,227. Complex pendulum-controlled steering mechanisms are used to overcome the tendency of these devices to climb the pipe walls during longitudinal movement through the pipe and to maintain carriage travel along the bottom of the pipe. Though possibly suitable for use in longer pipelines, these devices are also too complex for the rapid inspection of welds, particularly in a shop environment during the fabrication of short sections.

Thus, the prior art discloses no device which is simple, reliable and easy to use for the rapid x-ray examination of a few welds in a relatively short section of pipe. Further, there exists a need for a device which is readily adaptable for use in pipes of varying diameters and ranges of wall thicknesses for each diameter.

SUMMARY OF THE INVENTION

The present invention provides a pipe inspection probe carrier which is inherently self-centering as it is manually moved along a pipe interior into position for x-ray examination of a circumferential weld. The probe carriage is mounted on laterally spaced pairs of ball transfers which, because of their omnidirectional rolling capability, will always cause the carriage to roll to and remain at the bottom of the cylindrical pipe, even if the carriage is moved through a horizontal bend. A centrally mounted probe fixture carries the x-ray probe and is adjustable to set the probe coincident with the centerline of the pipe to be examined and, because the probe setting is established with respect to the surface of the ball transfers in contact with the pipe surface, the probe also remains centered. Operator access to the point of the weld to assure alignment of the probe is obviated and the inherent self-centering of the probe allows the use of panoramic x-ray techniques in which an entire circumferential weld can be shot in one exposure.

DESCRIPTION OF THE PREFERRED EMBODIMENT

Figure 2:
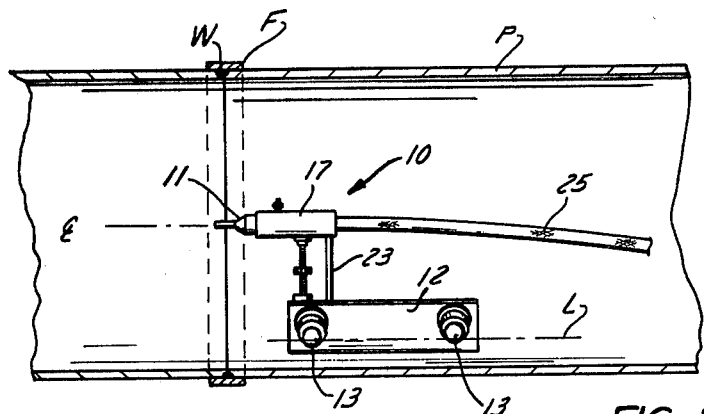
FIG. 2 is a side elevation of the probe carrier of FIG. 1.
Figure 1:
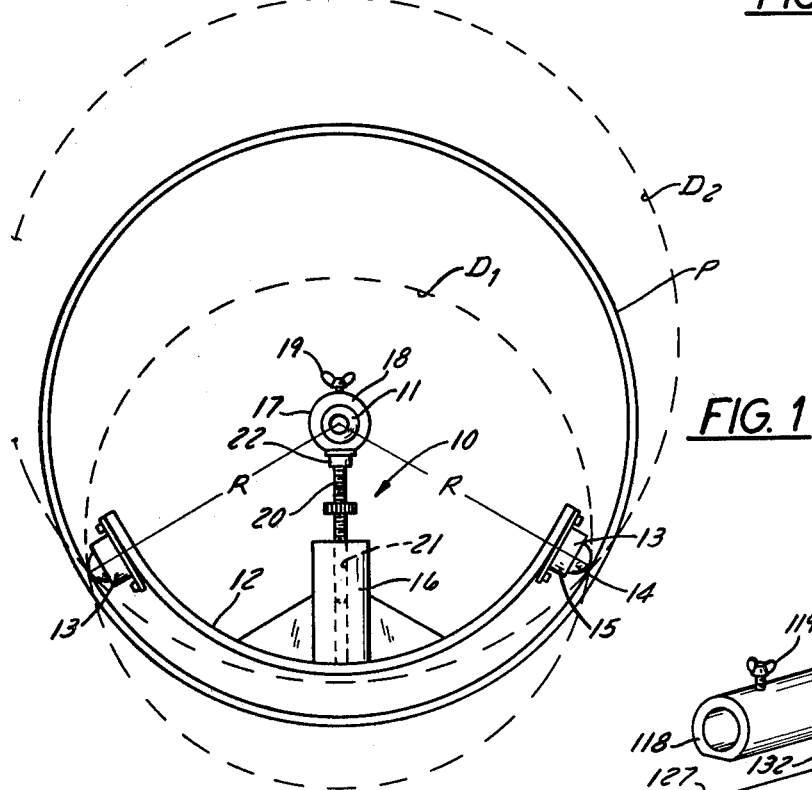
FIG. 1 is a front view of the x-ray probe carrier of the present invention shown with the probe mounted therein and positioned within a pipe section.

FIG. 1 shows the self-centering x-ray probe carrier 10 of the present invention positioned at the bottom of the inside of a section of pipe P to be inspected. The x-ray probe 11 is set to lie on the centerline of the pipe and the carrier 10 is moved along the pipe to locate the probe at a weld joint W, as shown in FIG. 2. The x-ray procedure itself is well known in the art and comprises wrapping a length of film F around the outside of the pipe over the weld. A single burst of radiation from the x-ray probe 11 exposes the film and provides a single x-ray of the entire circumferential weld joint.

Figure 3:
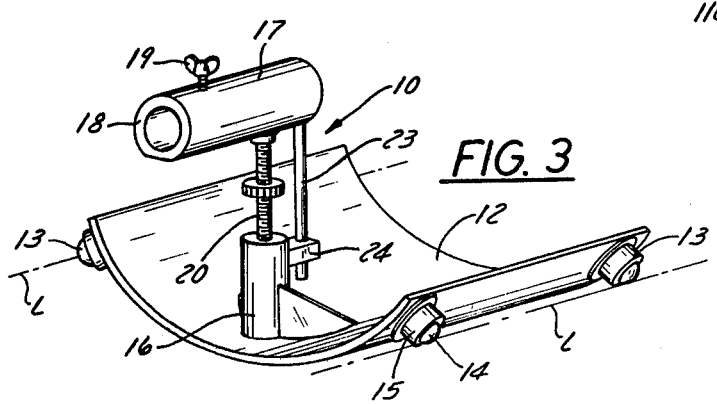
FIG. 3 is a perspective view of the probe carrier.

Referring also to FIG. 3, the probe carrier 10 includes a carriage 12 which, in the preferred embodiment, is made from a semicylindrical section of pipe. Attached to the underside of the carriage 12 to support the same for movement along the bottom of the pipe are laterally spaced pairs of ball transfers 13. The ball transfers are preferably disposed as close as practicable to the lateral edges of the carriage 12 to maximize stability and the pairs of ball transfers at each edge are disposed on lines parallel to the centerline of the pipe P. The ball transfers may be of the standard commercially available type, each comprising a ball 14 mounted for omnidirectional rotation in a housing 15.

A probe fixture 16 is centrally mounted on the upper surface of the carriage 12 and preferably near the front edge thereof. A probe holder 17 is adjustably attached to the probe fixture 16 for vertical movement toward and away from the probe fixture. The upper portion of the probe holder 17 includes a horizontally disposed, hollow cylindrical tube 18 into which the x-ray probe 11 is adapted to be inserted and held coaxially therein, as with a set screw 19.

Vertical adjustment of the probe holder 17 with respect to the probe fixture 16 is provided by an adjusting screw 20 mounted in a vertical threaded bore 21 in the probe fixture. The upper end of the adjusting screw is rotatably held in a swivel 22 fixed to the underside of the cylindrical tube 18. In this manner, the tube 18 may be held against rotation in a horizontal plane as the adjusting screw 20 is rotated to effect vertical adjustment. Preferably, an anti-rotation means is also provided to prevent horizontal rotation of the cylindrical tube 18 during vertical adjustment. To this end, a guide rod 23 may be attached to the underside of the tube 18 to extend vertically downward therefrom parallel to the adjusting screw 20. The guide rod is slidably disposed for free vertical movement in a guide bracket 24 fixed to the probe fixture 16, but the guide rod and the cylindrical tube 18 to which it is attached are prevented from rotating in a horizontal plane.

As indicated above, the ball transfers 13 are mounted on the carriage 12 such that the line defined by the surface contact points of the balls 14 of each lateral pair is parallel to the line similarly defined by the opposite pair, as shown by lines L in FIGS. 2 and 3. Referring also to FIG. 1, it will be seen that, over a wide range of pipe internal diameters defined by certain structural limits of the carrier 10, the ball transfers 13 will inherently assume a position such that the lines L always coincide with the inner cylindrical surface of the pipe P and are parallel to the centerline of the pipe and perpendicular to the plane of the circumferential weld W. The approximate range of pipe internal diameters within which the carrier is operable is shown schematically by the dashed lines $D_1$ and $D_2$ in FIG. 1. Further, with the carrier so positioned within a pipe, the probe holder 17 is inherently disposed in a plane through the pipe centerline equidistant from the lines L. Adjustment of the probe holder in either direction is restricted to movement in that plane by the operation of the guide rod 23 in the bracket 24.

The probe 11 is attached to the end of a control line 25 which, as is well known in the art, is used to move an x-ray source from a shielded container to the tip of the probe where the source is held for a period of time to expose the film to radiation. The shielded container is preferably located outside the end of the pipe section, but may also be within the probe itself. The control line 25 may also be used by the operator of the x-ray device to move and position the carrier from a location outside the pipe.

The x-ray probe carrier 10 is quite simply adjusted and operated in the following manner. Having determined the internal diameter (I.D.) of the pipe to be inspected, the probe holder 17 is moved up or down by turning the adjusting screw 20 to set the tip of the x-ray probe 11 (or the centerline of the cylindrical tube 18, if the probe has not yet been mounted) at a distance from the outer surface of one of the balls 14 of a ball transfer 13 equal to the radius of the pipe I.D. The radius (R in FIG. 1) is most conveniently measured from either of the ball transfers laterally adjacent to the probe holder 17 near the forward edge of the carriage 12. With the x-ray probe 11 mounted in the holder tube 18 and secured with the set screw 19, the carrier is simply pushed along the bottom of the pipe a measured distance to the weld to be x-rayed. The radiation source is moved from the shielded container to the tip of the probe, held there for an appropriate exposure time, and then retracted to the container. A succession of welds in a pipe section may, of course, be sequentially x-rayed by relocating the carrier in the same manner.

Because of the inherently self-centering characteristic of the carrier, the operator is assured that the x-ray probe will always remain on the pipe centerline. The carrier may be pushed or pulled through a horizontal pipe bend and will automatically realign itself in the same centered position. The omnidirectional nature of the ball transfers will always tend to maintain the carrier at the bottom of the pipe, both when moving and at rest. However, even if the carrier were to ride up the pipe wall slightly, because of an inbalance in the carrier or a lateral component in the force used to position the carrier, the probe will remain centered.

The x-ray probe carrier disclosed herein is extremely well suited for use in examining welds where a wide range of pipe diameters or pipe schedules is regularly encountered in production. A typical carrier 10 made in accordance with the construction of the above described preferred embodiment may, for example, be used in standard pipe sizes 12 to 18 having nominal outside diameters ranging, respectively, from 12.75 to 18.0 inches. In addition, however, there may be a dozen or more "schedules" or different wall thicknesses for each nominal pipe size, providing about 50 potentially different I.D. dimensions to be accommodated by a single probe carrier. The simple and rapid adjustment of the probe holder makes the device of this invention ideally suited for widely varying pipe sizes and schedules.

Figure 4:
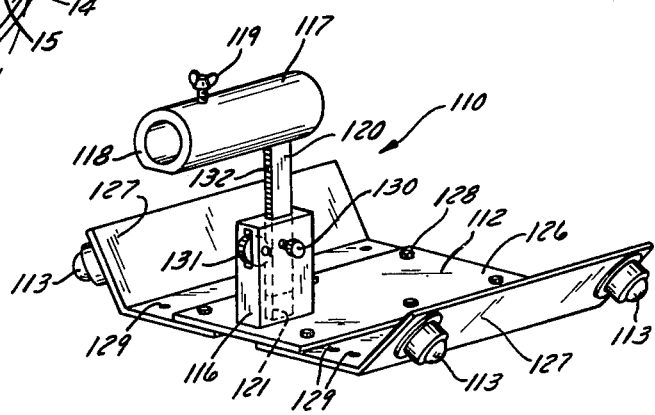
FIG. 4 is a perspective view of an alternate embodiment of the invention.

In FIG. 4, there is shown an alternate embodiment of the invention in which a carrier 110 has an adjustable carriage 112 to adapt the device for use with an even greater range of pipe diameters. The carriage 112 includes a center platform 126 and two identical lateral wings 127, to each of which is attached a pair of ball transfers 113. The wings 127 are adjustably attached to the center platform 126 to vary the width of the carriage by, for example, bolts 128 extending through holes in the platform and a selected set of matching holes from a laterally aligned series 129 in each wing. The probe fixture 116 is centrally attached to the carriage 112 and includes a vertical rectangular slot 121 adapted to receive a rectangular height adjustment bar 120 of the probe holder 117. The probe holder includes a cylindrical tube 118 and set screw 119, both of which may be identical to those of the preferred embodiment. The rectangular configuration of the mating adjustment bar 120 and slot 121 prevents rotation of the cylindrical tube 118 in a horizontal plane without the need for any supplemental anti-rotation means. Vertical adjustment of the probe holder 117 may be effected by merely sliding the adjustment bar to the proper position and setting the locking screw 130. Alternately and as shown, a thumb wheel 131 and rack 132 may be used for height adjustment. Otherwise, the carrier 112 of FIG. 4 is operated in the same manner as that of the preferred embodiment.

We claim:

1. An apparatus for transporting and locating a probe for examination of a circumferential weld joining two sections of cylindrical pipe comprising:
   a. a carriage for supporting the examination probe;
   b. a pair of ball transfers attached to the underside and adjacent each lateral edge of the carriage, with the line defined by each pair of ball transfers lying parallel to the pipe centerline, to support the carriage for longitudinal movement along the bottom inside surface of a pipe section;
   c. a probe fixture centrally mounted on the carriage and having a probe holder adjustably attached thereto; and,
   d. probe height adjustment means attached to and extending downwardly from the probe holder into the probe fixture, the height adjustment means being manually operable for vertical movement with respect to the probe fixture for selective positioning in a plane through the pipe centerline equidistant from the ball transfers.

2. The apparatus of claim 1 wherein the carriage comprises a semicylindrical section of pipe.

3. The apparatus of claim 1 wherein the probe height adjustment means comprises a threaded screw adapted to cooperate with a threaded bore in the probe fixture.

4. The apparatus of claim 1 including anti-rotation means interconnecting the probe holder and the probe fixture for preventing rotation of the probe holder in a plane perpendicular to the vertical axis of the probe height adjustment means.

5. The apparatus of claim 4 wherein the anti-rotation means is integral to the probe height adjustment means.

* * * * *